United States Patent [19]

Frensch et al.

[11] 4,144,050

[45] Mar. 13, 1979

[54] MICRO GRANULES FOR PESTICIDES AND PROCESS FOR THEIR MANUFACTURE

[75] Inventors: Heinz Frensch; Konrad Albrecht; Klaus Hook, all of Frankfurt am Main, Fed. Rep. of Germany

[73] Assignee: Hoechst Aktiengesellschaft, Frankfurt am Main, Fed. Rep. of Germany

[21] Appl. No.: 779,539

[22] Filed: Mar. 21, 1977

Related U.S. Application Data

[63] Continuation of Ser. No. 547,582, Feb. 6, 1975, abandoned, which is a continuation of Ser. No. 8,095, Feb. 2, 1970, abandoned.

[30] Foreign Application Priority Data

Feb. 5, 1969 [DE] Fed. Rep. of Germany ....... 1905524

[51] Int. Cl.$^2$ .................... A01N 9/20; A01N 9/00; A01N 9/12; A61K 31/74
[52] U.S. Cl. .................................. 71/120; 71/65; 71/97; 424/276; 424/288; 424/322; 424/349; 424/23; 424/78
[58] Field of Search .................. 424/288, 23, 276, 322, 424/349; 71/65, 97, DIG. 1, 120

[56] References Cited

U.S. PATENT DOCUMENTS

| | | | |
|---|---|---|---|
| 3,149,953 | 9/1964 | Miller | 71/2.4 |
| 3,157,486 | 11/1964 | Harrison et al. | 71/2.4 |
| 3,382,150 | 5/1968 | Grass et al. | 424/23 |
| 3,617,246 | 11/1971 | Duyfjes et al. | 71/79 |
| 3,657,446 | 4/1972 | Blackmore | 424/274 |
| 3,737,551 | 6/1973 | Karsten et al. | 424/286 |
| 3,791,811 | 2/1974 | French et al. | 71/120 |

*Primary Examiner*—Albert T. Meyers
*Assistant Examiner*—D. W. Robinson
*Attorney, Agent, or Firm*—Curtis, Morris & Safford

[57] ABSTRACT

The invention is concerned with micro granules for pesticides and their manufacture by wet grinding a suspension of the active compound together with adjuvants in a ball mill to a particle size of at most 0.01 mm and subsequent spray-drying of the suspension thus obtained under a pressure of from 5 to 8 atmospheres gauge and at 140° to 300° C.

2 Claims, No Drawings

MICRO GRANULES FOR PESTICIDES AND PROCESS FOR THEIR MANUFACTURE

This is a continuation of application Ser. No. 547,582 filed Feb. 6, 1975 which is a continuation of application Ser. No. 8,095 filed Feb. 2, 1970, both now abandoned.

The present invention relates to micro size granules for use in plant protection and to a process for their manufacture.

In order also to rationalize the use of plant protecting agents there is a demand for bringing out products of a higher concentration than has been hitherto usual. This means a distribution of smaller volumes of formulated pesticides per unit of cultivated area. Conventional granules for pesticidal purposes have a particle size of about 0.5 to 1.5 mm.

This invention provides micro granules for pesticides which comprise a homogeneous content of a solid pesticidal active ingredient within a particle size range of from 0.075 to 0.4 mm, in addition to inert substances, wetting agents, dispersing agents and adhesion-promoting agents as well as, optionally, a protective colloid.

Another object of this invention is a process for the manufacture of micro granules for pesticides of a granular size of from 0.075 to 0.4 mm, which comprises grinding pesticides in wet state together with inert substances, wetting and dispersing agents, adhesion-promoting agents and, optionally, protective colloids in ball mills to yield a particle size of a maximum of 0.01 mm, preferably of about 0.005 mm, and spray-drying the suspensions or pastes thus obtained by means of rotating disks at a circumferential speed of from 80 to 100 m/sec., preferably using single feed nozzles under a spraying pressure of from 5 to 8 atmospheres gauge, or double feed nozzles under a spraying pressure of from 0.5 to 4 atmospheres gage, preferably from 0.5 to 1.5 atmospheres gauge, at a drying gas inlet temperature of from 300 to 140° C., preferably from 270 to 180° C., and at a drying gas outlet temperature of from 50 to 120° C., preferably from 60 to 80° C.

The active ingredient particles in the micro granules have a size of from 0.001 to 0.010 mm, advantageously of up to 0.005 mm.

Owing to the above-mentioned small size of the granules and hence a better distribution density to be achieved per unit of area, the active ingredients concentration in the granules can be increased to a content of 80%, preferably of from 2 to 20%, depending on the method of bringing out and the intended use. Alternatively, compared with conventional granules, the granules of the invention having the same concentrations of active ingredient permit a better distribution effect which can still be increased by the fine size and homogeneity of the active ingredient particles within the separate granules. In comparison to known sprays and spraying liquors, the granules of the invention can be brought out more accurately owing to their weaker tendency to wind drift which avoids damage to neighboring cultures, as may especially result from the use of herbicides. Moreover, it is possible, as also in the case of coarse particles, to bring out the granules accurately, for example in flooded rice cultures. The novel granules may also be spread out with the seeds by the drill or band method.

The process of the invention allows granulation of all solid pesticidal active ingredients, for example herbicidal, insecticidal and fungicidal compositions, together with the inert material to be advantageously used for maintaining their chemical stability and their biological activity, for example diatomacious earth, silicic acids, kaolinite-containing quartz, alumina, chalk, bentonites, atta-clay, inorganic salts, milk powder or starch.

An addition of dispersing and wetting agents, for example sodium or ammonium salt of lignine-sulfonic acid, sodium salt of dinaphthylmethane-disulfonic acid, sodium salt of butylnaphthalene-sulfonic acid, oleylmethyl tauride sodium, sodium salt of an alkylphenylsulfonic acid, or condensation products of fatty acids and albumin permits a uniform distribution, wetting and release of the active ingredient particles. Depending on the type and dosage of adhesion-promoting agents, advantageously sodium salt of lignine-sulfonic acid, polyvinyl acetate, polyvinyl acetate copolymers and partially hydrolized polyvinyl alcohols or carboxymethyl cellulose having various polymerization degrees, vegetable rubber or glues, the release of the active ingredient can be accelerated or delayed.

It is not possible to prepare granules of the disclosed fine size according to known methods, for example by adhesion of active ingredients to inert substance granules or by means of granulating cylinders. Neither can the granules of the desired particle size be obtained with a reasonable yield by subsequent grinding of coarse granules of known constitution.

According to the process of the invention, it is advantageous first to grind active ingredient concentrates in wet state in an aqueous suspension by means of friction ball mills to obtain a particle size of a maximum of 0.01 mm. The ground material is then stirred together with the above-cited additives in water into suspensions or pastes having a dry material content of from 40 to 70%. By incorporating a large amount of sodium or ammonium salt of lignine-sulfonic acid these can be maintained in a freely flowing state.

The process of the invention yields micro granules in an amount of from 80 to 90% and a particle size of from 0.075 to 0.4 mm.

The granules are separated by means of cyclones. The portions of from 10 to 20% of finest particles may be separated and granulated once more.

The granules of the invention have good flow properties.

The following examples serve to illustrate the invention, the parts and percentages being by weight unless stated otherwise.

EXAMPLE 1

Micro granules of pentachloronitro-benzene having an active ingredient content of 80%

(a) A mixture of 40 parts of pentachloronitro-benzene, 9 parts of sodium salt of lignine-sulfonic acid, 1 part of partially hydrolized polyvinyl acetate and 50 parts of water was ground in wet state in a friction ball mill to yield a grain size of from 1 to 5 microns; the paste or suspension thus obtained was then spray-dried in a drying tower by means of a single feed nozzle at a pressure of from 7 to 8 atmospheres gauge at an air inlet temperature of 240° C. and an air outlet temperature of 75° C. 82 to 85% of the finest particles obtained had a size of from 0.075 to 0.350 mm. The content of active ingredient was 80%.

(b) Micro granules obtained according to the above method were mixed with 0.4 parts of a polyvinylacetate copolymer to slow down the release of the active ingredient.

EXAMPLE 2

Micro granules of pentachloronitro-benzene having an active ingredient content of 50%

A paste or suspension obtained according to Example 1 was stirred with further 1 part of partially hydrolized polyvinylacetate or 1 part of carboxymethyl cellulose, 5 parts of sodium salt of lignine-sulfonic acid, 24 parts of kaolinite-containing quartz powder or alumina and 5 parts of water and the mixture was spray-dried as disclosed above. The micro granules obtained had a size of from 0.075 to 0.4 mm and an active ingredient content of 50%.

EXAMPLE 3

Micro granules of pentachloronitro-benzene having an active ingredient content of 10%

A paste or suspension obtained according to Example 1 was stirred with further 5 parts of sodium salt of dinaphthyl-methanedisulfonic acid, 50 parts of sodium salt of lignine-sulfonic acid, 20 parts of sodium sulfate, 4 parts of carboxymethyl cellulose, 271 parts of bentonite or kieselguhr and 280 parts of water; this suspension having a solids content of 55% was spray-dried by means of a double feed nozzle at a spraying pressure of from 0.5 to 0.6 atmosphere gauge at a drying air inlet temperature of 250° C. and a drying air outlet temperature of 75° C.

85% of the granules obtained had a size of from 0.075 to 0.4 mm and an active ingredient content of 10%.

EXAMPLE 4

Micro granules of linuron having an active ingredient content of 10%

In a manner analogous to Example 1, a paste or suspension containing 40% of linuron was prepared. This was stirred with further 35 parts of sodium salt of lignine-sulfonic acid, 3.5 parts of partially hydrolized polyvinylacetate, 311.5 parts of kaolinite-containing quartz powder (or a mixture of 187 parts of kieselguhr and 124.5 parts of sodium hyperphosphate) and 215 parts of water in a colloidal mill. The suspension thus obtained having a solids content of 60% was spray-dried. The yield of micro granules having a particle size of from 0.075 to 0.35 was 85%. The active ingredient content was 10%.

By adding from 0.1 to 1.5 parts of polyvinyl acetate in dispersed form the granules obtained had a slower release of active ingredient.

EXAMPLE 5

Micro granules of monolinuron having an active ingredient content of 10%

The suspension was prepared in a manner analogous to Example 4 using monolinuron instead of linuron.

EXAMPLE 6

Micro granules of monolinuron having an active ingredient content of 20%

A paste or suspension obtained by grinding in wet state a mixture of 20 parts of monolinuron, 10 parts of partially hydrolized polyvinyl acetate, 15 parts of sodium salt of ligninesulfonic acid, 20 parts of kieselguhr, 35 parts of sodium hyperphosphate and 70 parts of water was spray-dried by means of a single feed nozzle at a pressure of from 7 to 8 atmospheres gauge and at an air inlet temperature of 260° C. and an air outlet temperature of 70° C. The yield of finest particles having a size of from 0.075 to 0.4 mm was 87% and the active ingredient content was 20%.

EXAMPLE 7

Micro granules of diuron having an active ingredient content of 10%

The suspension was prepared in a manner analogous to Example 4 using diuron instead of linuron.

EXAMPLE 8

Micro granules of endosulfane having an active ingredient content of 20%

A paste or suspension obtained by grinding in wet state a mixture of 20 parts of endosulfane, 15 parts of sodium salt of lignine-sulfonic acid, 2 parts of sodium salt of dibutylnaphthylsulfonic acid, 0.1 part of sodium salt of dodecyl-benzene-sulfonic acid, 0.5 part of partially hydrolized polyvinyl acetate, 10 parts of sodium sulfate, 52.4 parts of kieselguhr (pH of 7.5) and 70 parts of water the solids content being 59%, was spray-dried by means of a double feed nozzle under a pressure of 0.7 atmosphere gauge at a drying air inlet temperature of 250° C. and a drying air outlet temperature of 70° C. The yield of micro granules having a size of from 0.075 to 0.35 mm was 88%. The active ingredient content was 20%.

EXAMPLE 9

Micro granules of triphenyl tin acetate having an active ingredient content of 20%

(a) In a manner analogous to Example 8, but at a nitrogen inlet temperature of 240° C. and a nitrogen outlet temperature of 70° C. a paste or suspension obtained by grinding in wet state a mixture of 20 parts of triphenyl-tin-acetate, 15 parts of sodium salt of lignine-sulfonic acid, 0.5 part of sodium salt of dodecyl-benzene-sulfonic acid, 21 parts of chalk, 10.5 parts of kaolinite-containing quartz, 20 parts of sodium hyperphosphate, 3 parts of partially hydrolized polyvinyl acetate, 10 parts of milk powder and 70 parts of water was spray-dried by means of a double feed nozzle. The yield of micro granules having a particle size of from 0.1 to 0.4 mm was 82%.

(b) In a manner analogous to (a), a paste or suspension of the following constitution: 20 parts of triphenyl tin chloride, 20 parts of sodium salt of lignine-sulfonic acid, 0.5 parts of sodium salt of dodecyl-benzene-sulfonic acid, 4 parts of partially hydrolized polyvinyl acetate or carboxymethyl cellulose, 25 parts of milk powder, 15 parts of sodium hyperphosphate, 15.5 parts of chalk or magnesium carbonate and 70 parts of water was spray-dried. The yield of micro granules having a particle size of from 0.1 to 0.4 mm was 80% and the active ingredient content was 20%.

We claim:

1. A process for the manufacture of a microgranular pesticide composition which comprises preparing a suspension of 2 to 80% by weight of a solid, particulate pesticidally active compound with (i) inert substance selected from the group consisting of diatomacious earth, silicic acids, kaolinite, alumina, chalk, bentonites, atta-clay, inorganic salts, milk powder and starch, (ii) wetting and dispersing agent in an amount of between 10% and 20% by weight, selected from the group consisting of sodium salt of lignine-sulfonic acid, ammonium salt of lignine-sulfonic acid, sodium salt of dinaphthylmethane-disulfonic acid, sodium salt of butylnaphthalene-sulfonic acid, oleylmethyl tauride sodium, sodium salt of alkyphenylsulfonic acid, condensation products of fatty acids, and albumin, and (iii) adhesion-promoting agent in an amount of between 0.5 to 10% by weight selected from the group consisting of polyvinyl acetate, polyvinyl acetate copolymers, partially hydrolyzed polyvinyl alcohols, carboxymethyl cellulose, vegetable rubbers, and glues, the total of said ingredients being 40 to 70 parts by weight in 30 to 60 parts by weight of water, wet grinding said suspension to a pesticide particle size no greater than 0.01 mm and thereafter spray drying the wet suspension in a spray drying apparatus at a drying gas inlet temperature of from 140° to 300° C. and a drying gas outlet temperature of 50° to 120° C. by means of a rotating disc at a circumferential disc speed of 80 to 100 m/sec. or using a single feed spray nozzle at a spraying pressure of from 5 to 8 atmospheres gauge or a double feed spray nozzle under a spraying pressure of 0.5 to 4 atmospheres gauge, to produce a microgranular pesticidal composition largely composed of particles having a size of 0.075 to 0.4 mm.

2. A process for the manufacture of a microgranular pesticide composition which comprises preparing a suspension in 30 to 60 parts by weight of water of 40 to 70 parts by weight of a mixture comprising from 2 to 80% by weight of a pesticide selected from the group consisting of pentachloronitrobenzene, linuron, monolinuron, diuron, endosulfane, triphenyl-tin acetate and triphenyl tin chloride, together in a wet state in a ball mill with (i) inert substance selected from the group consisting of diatomacious earth, silicic acids, kaolinite, alumina, chalk, bentonites, atta-clay, inorganic salts, milk powder and starch (ii) wetting and dispersing agent in an amount of between 10% and 20% by weight selected from the group consisting of sodium salt of lignine-sulfonic acid, ammonium salt of lignine-sulfonic acid, sodium salt of dinaphthylmethane-disulfonic acid, sodium salt of butylnaphthalene-sulfonic acid, oleylmethyl tauride sodium, sodium salt of alkyphenylsulfonic acid, condensation products of fatty acids, and albumin, and (iii) adhesion-promoting agent in an amount of between 0.5% and 10% by weight selected from the group consisting of polyvinyl acetate, polyvinyl acetate copolymers, partially hydrolyzed polyvinyl alcohols, carboxymethyl cellulose, vegetable rubber and glues, wet grinding the suspension to yield a pesticide particle size of up to 0.01 mm and thereafter spray drying the wet suspension in a spray drying apparatus at a drying gas inlet temperature of from 140° to 300° C. and a drying gas outlet temperature of from 50° to 100° C. by means of a rotating disc at a circumferential disc speed of 80 to 100 m/sec. or using a single feed spray nozzle at a spraying pressure of from 5 to 8 atmospheres gauge or a double feed spray nozzle under a spraying pressure of 0.5 to 4 atmospheres gauge, to produce a microgranular pesticidal composition largely composed of particles having a size of 0.075 to 0.4 mm.

* * * * *